US006656928B1

(12) United States Patent
McCadden

(10) Patent No.: US 6,656,928 B1
(45) Date of Patent: Dec. 2, 2003

(54) COMPOSITION FOR THE TOPICAL TREATMENT OF RASHES, DERMATOSES AND LESIONS

(76) Inventor: Michael E. McCadden, 121 Whitebridge Meadows La., St. Louis, MO (US) 63141

( * ) Notice: Subject to any disclaimer, the term of this patent is extended or adjusted under 35 U.S.C. 154(b) by 0 days.

(21) Appl. No.: 09/652,381

(22) Filed: Aug. 31, 2000

Related U.S. Application Data

(60) Provisional application No. 60/152,067, filed on Sep. 2, 1999.

(51) Int. Cl.$^7$ .......................... A61K 31/59; A61K 31/56; A01N 43/50
(52) U.S. Cl. ....................... 514/167; 514/171; 514/396
(58) Field of Search .......................... 424/400; 514/396, 514/167, 171

(56) References Cited

U.S. PATENT DOCUMENTS

| 4,569,935 | A | * | 2/1986 | Rosenberg et al. ......... 514/252 |
| 5,110,809 | A | | 5/1992 | Wang et al. |
| 5,219,877 | A | | 6/1993 | Shah et al. |
| 5,478,814 | A | | 12/1995 | Packman |
| 5,972,920 | A | * | 10/1999 | Seidel ........................ 514/171 |

FOREIGN PATENT DOCUMENTS

| CN | 1095615 | * | 11/1994 |
| CN | 1111984 | * | 11/1995 |
| EP | 173478 | * | 3/1986 |
| WO | 9214472 | * | 9/1992 |
| WO | 9727862 | * | 8/1997 |

OTHER PUBLICATIONS

Kenneth A. Arndt et al. "Manual of Dermatologic Therapeutics" 5th Ed., Little, Brown & Co., pp. 49, 290, 309.
A. R. W. Bowring et al. "The Treatment of Napkin Dermatitis: a Double–Blind Comparison of Two Steroid–Antibiotic Combinations" Pharmatherapeutica, vol. 3, No. 9 (1984) pp. 613–617.
Roger C. Cornell et al. "Correlation of the Vasoconstriction Assay and Clinical Activity in Psoriasis" Arch Dermatol, vol. 121 (Jan. 1985) pp. 63–67.
E.G.V. Evans et al. "Does Naftifine Have Anti–Inflammatory Properties? A Double–blind Comparative Study With 1% Clotrimazole/1% Hydorcortisone in Clinically Diagnosed Fungal Infection of the Skin" British Journal of Dermatology, vol. 129 (1993) pp. 437–442.
Thomas B. Fitzpatrick et al. Dermatology in General Medicine, vol. II, 4th Ed., McGraw–Hill, Inc., (1993) pp. 2444–2447 and 2847.
Cynthia A. Guzzo et al. "Chapter 64, Dermatological Pharmacology" Goodman & Gilman's The Pharmacological Basis of Therapeutics, 9th Ed., McGraw–Hill (1996) pp. 1593–1598.

Steven K. Hebel et al., "Drug Facts and Comparisons" Facts and Comparisons, St. Louis, A Wolters Kluwer Company (Jan. 2000) pp. ii, 1658, 1659, 1684.
David B. Jackson et al. "Bioequivalence (bioavailability) of General Topical Corticosteroids" Journal of the American Academy of Dermatology, vol. 20, No. 5, Pt. 1 (May 1989) pp. 791–796.
G.V. Jaffe et al., "An Open Trial of Clotrimazole Plus Hydrocortisone Cream in the Treatment of Napkin Dermatitis in General Practice" Pharmatherapeutica, vol. 4, No. 5 (1985) pp. 314–318.
H. Irving Katz et al. "SCH 370 (Clotrimazole–Betamethasone Dipropionate) Cream in Patients with Tinea Cruris or Tinea Corporis" vol. 34 (Aug. 1984) pp. 183–188.
Sandra Levy "Latest Switch—Lamisil—Offers to Get it Done Faster" Drug Topics, Apr. 19, 1999, pp. 72.
A. W. McKenzie et al. "Method for Comparing Percutaneous Absorption of Steroids" Archive of Dermatology, vol. 86, (1962) pp. 608–610.
Virgil A. Place et al. "Precise Evaluation of Topically Applied Corticosteroid Potency" Archives of Dermatology, vol. 101 (May 1970) pp. 531–537.
G. S. Shankland et al. "Comparative–in–vitro Activity of Clotrimazole and a Clotrimazole/hydrocortisone Combination in the Treatment of Experimental Dermatophytosis in Guinea Pigs" Journal of Antimicrobial Chemotherapy, vol. 25 (1990) pp. 825–830.
Richard E. Stoughton "Are Generic Formulations Equivalent to Trade Name Topical Glucocorticoids?" Archives of Dermatology, vol. 123 (Oct. 1987) pp. 1312–1314.
Richard E. Soughton "Bioassay System for Formulations of Topically Applied Glucocorticosteriods" Archives of Dermatology, vol. 106 (Dec. 1972) pp. 825–827.
Richard E. Soughton "Vasoconstrictor Activity and Percutaneous Absorption of Glucocorticosteriods" Archives of Dermatology, vol. 99 (Jun. 1969) pp. 753–756.
"USP 24, NF 19" U.S. Pharmacopeia & National Formulary, The United States Pharmacopeial Convention, Inc. 12601 Twinbrook Parkway, Rockville, MD (1999) pp. 273–274, 1768–1769.
Paul Walsh et al. "Schering, Lotrisone" Physicians' Desk Reference PDR 55ed 2001, pp. 2912–2914.
Martin H. Wortzel A Double–Blind Study Comparing the Superiority of a Combination Antifungal (Clotrimazole)/Steroidal (Bethamethasone Dipropionate) Product, CUTIS, vol. 30, (Aug. 1982) pp. 258–261.

* cited by examiner

*Primary Examiner*—Alton N. Pryor
(74) *Attorney, Agent, or Firm*—Senniger, Powers, Leavitt & Roedel

(57) ABSTRACT

Composition for topical administration comprising (a) a corticosteroid, (b) a drying agent, and (c) a broad spectrum anti-fungal agent that treats both dermatophytes and yeast.

57 Claims, No Drawings

COMPOSITION FOR THE TOPICAL TREATMENT OF RASHES, DERMATOSES AND LESIONS

REFERENCE TO RELATED APPLICATIONS

This application claims priority from provisional application Ser. No. 60/152,067 filed Sep. 2, 1999.

BACKGROUND OF THE INVENTION

The present invention relates to a composition for the treatment of rashes, dermatoses or lesions, which are known to be treated topically to improve or favorably alter the disease condition. Such rashes, dermatoses or lesions include acute, inflammatory reactions of the skin resulting from exposure to an adverse local environment (e.g., diaper rash, intertrigo, lichen simplex chronicus, balanitis, balanoposthitis), rashes, dermatoses or lesions caused by a fungal or yeast infection (e.g., tinea cruris, tinea pedis, tinea corporis, tinea versicolar, Candidal infections), rashes, dermatoses or lesions caused by an allergic or irritant reaction (such as that caused by poison ivy, poison oak or poison sumac, or other forms of contact dermatitis), rashes, dermatoses or lesions of a chronic nature (e.g. seborrheic dermatitis, psoriasis, atopic dermatitis) or caused by infection, irritation or aggravation of another condition such as occurs with acne, and other rashes, dermatoses or lesions.

Diaper rash is an irritant contact dermatitis, often secondarily infected with Candida organisms. It occurs as a result of constant exposure to an adverse local environment. Constant dampness is the main causative event, but numerous irritants add to the problem, including feces, urea, intestinal enzymes, detergent in the diaper, and even some medications. Moisture from the diaper further weakens the skin barrier, making the rash worse. The rash is often very red, may become raw, and can be quite painful for the child. Erythematous papules, vesicles or erosions, oozing, and ulceration may occur.

A variety of methods exist for treating diaper rash, including hydrocortisone cream (1% by weight), zinc oxide ointment, undecylenic acid, zinc undecylenate, nystatin cream, clotrimazole cream, or miconazole cream. Individually these therapies do not treat both the irritant dermatitis and the secondary Candida or dermatophyte infection.

Bowring et al (Bowring A W, Mackay D, Taylor F R: "The treatment of napkin dermatitis: a double-blind comparison of two steroid-antibiotic combinations," *Pharmatherapeutica* (1984) vol. 3, #9; 613–617) compared a composition containing miconazole (2% by weight) and hydrocortisone (1% by weight) with a composition containing nystatin (100,000 i.µ./gm), benzalkonium chloride (0.2% by weight), dimethicone (10% by weight), and hydrocortisone (0.5% by weight) in a study of 62 infants with moderate to severe diaper rash. Clinical assessments were made of erythema, weeping, tissue maceration, and infant irritability. Both treatments were reported to produce a high and similar overall cure rate (80% and 84% respectively), with a significant improvement within 48 hours in the majority of cases. While these results are encouraging, a more rapid and complete clinical response is desired.

Shankland et al.(Shankland G S, Richardson M D: "Comparative in-vivo activity of clotrimazole and a clotrimazole/hydrocortisone combination in the treatment of experimental dermatophytosis in guinea pigs," *Journal of Antimicrobial Chemotherapy* (1990) 25, 825–830), describe the use of formulations containing hydrocortisone and clotrimazole for the treatment of dermatophyte infections Guinea pigs infected with *Trichophyton mentagrophytes var. mentagrophytes* were treated with once daily application of 1% by weight clotrimazole alone, 1% by weight hydrocortisone alone, base alone, a combination of 1% by weight clotrimazole and 1% by weight hydrocortisone, or no treatment at all. Clinically, the animals receiving combination therapy (clotrimazole plus hydrocortisone) were reported to have improved most quickly and cultures were negative after two treatments. Histological examination showed resolution of the infection and little inflammation.

An open, non-comparative study was performed to assess the effectiveness, acceptability and tolerability of a 1% by weight clotrimazole plus 1% by weight hydrocortisone cream in the treatment of 112 infants with napkin dermatitis (diaper rash) (Jaffe G V, Grimshaw J J: "An open trial of clotrimazole plus hydrocortisone cream in the treatment of napkin dermatitis in general practice," *Pharmatherapeutica*, (1985), 4, 314–318). There was significant improvement in erythema, irritation and pustulation in all but a few patients, and 92% of the patients were considered to have been cured or markedly improved after 7 to 14 days of twice daily application. Again, while these results are encouraging, a more rapid and complete clinical response is desired.

A variety of methods have been used for the treatment of fungal infections including the use of potassium iodide, Castellani's paint, gentian violet, Whitfield's ointment, undecylenic acid, antibiotics (e.g. nystatin, fungizone and amphotericin B), griseofulvin, the imidazole antifungal agents such as miconazole, clotrimazole, econazole, ketoconazole, oxiconizole and sulconazole, the allylamine antifungal agents such as naftifine and terbinafine, the benzylamines such as butenafine HCl, the hydroxypyridone agents such as ciclopirox, the chlorinated iodopropynyl trichlorophenyl ether agents such as haloprogin, as well as tolnaftate, thymol, and tinver. Nystatin, fungizone, naftifine, and terbinafine, however, are only effective against yeast (Candida) and the imidazole compounds while effective in treating both dermatophytes and yeasts (Arndt, Kenneth A., *Manual of Dermatologic Therapeutics*, 5$^{th}$ edition, 1995, Little, Brown and Co., page 290) often do not provide rapid relief.

The fungal infections are commonly associated with signs of erythema and scaling and with symptoms of itching or painful burning. Clinical treatment for fungal disease requires at least two to four weeks for complete relief of symptoms. More recently, it has been found that fungal infections can be effectively treated with a combination product containing corticosteroids and imidazole antifungal agents (see above referenced studies). It is known that the sensitivity of fungal organisms varies with their life cycles; spores are more resistant to treatment than are mycelia. Steroids may induce fungal spores to produce mycelia, thereby making them more sensitive to treatment. Also, steroids are known to produce vasoconstriction at the site of application. This activity may delay or prevent the elimination of the antifungal agent from the application site, permitting the antifungal agent to remain in the epidermis for longer periods of time. It is therefore believed that a locally applied anti-inflammatory agent would offer direct and immediate relief for the inflammatory component of the lesion. The combination product should then provide fast relief of symptoms and eradicate the infection. Based on this concept, certain combinations of an antifungal agent and an anti-inflammatory agent have recently been developed for treatment of fungal disease. Currently, the commercially available combination products using this concept are Lotrisone cream (clotrimazole 1% by weight/betamethasone dipropionate 0.05% by weight), Daktacort cream (miconazole nitrate 2% by weight/hydrocortisone 1% by weight) and Canesten HC cream (clotrimazole 1% by weight/hydrocortisone 1% by weight).

It has been reported Lotrisone cream was therapeutically and mycologically better than clotrimazole 1% by weight and betamethasone dipropionate 0.05% by weight alone. See e.g., Wortzel, M.Y., H., Cutis 30: 258 (1982) and Katz et al. Cutis, 34(2), 183–8 (1984). Notwithstanding its clinical advantages, Lotrisone cream possesses some undesirable attributes. It contains a rather strong fluorinated steroid, betamethasone dipropionate, which can be cutaneously dangerous to use in intertrigious regions for extended periods. Potential side effects include skin atrophy, rebound phenomenon, telangiectasia, and danger to infants and small children due to possible suppression of the hypothalamic-pituitary-adrenal axis if used it too large a quantity. The corticosteroid triamcinalone is also a fluorinated steroid. It is mixed with nystatin in Mycolog. Triamcinalone possess the same risks as betamethasone dipropionate listed above.

Other marketed combination products of this type, e.g. Daktacort cream and Canesten HC cream, are combinations of low-potency steroids and imidazoles in a cream form. Such combination products in this cream vehicle often fail to provide the fast relief of the inflammatory symptoms which is normally desired for the treatment of a fungal infection, especially when the eruption is acutely inflamed, moist, and/or in an intertriginous area.

None of the above agents' vehicles provide rapid drying of a moist, oozing rash while helping to absorb further moisture and keep the skin dry, and at the same time treat both the irritant dermatitis and secondary Candida or dermatophyte infection.

There are several other papulosquamous skin diseases that can present and behave in a similar fashion to diaper dermatitis. These include intertrigo, tinea versicolar, contact dermatitis such as poison ivy and others, Candida skin infections, seborrheic dermatitis, inverse psoriasis, interdigital tinea pedis, tinea cruris, genital lichen simplex chronicus, balanoposthitis, balanitis, and others. All of these conditions (except tinea versicolar) can present with an intertriginous rash that can become moist, weeping, and quite irritated. The non-fungal rashes can also become secondarily infected with Candida and/or dermatophyte fungi. Current therapeutic options do not always clear these conditions as rapidly as desired.

SUMMARY OF THE INVENTION

Among the objects of the present invention, therefore, is the provision of a composition for topical treatment of rashes, dermatoses and lesions, the provision of such a composition which is easily applied to the skin, the provision of such a composition which contains a corticosteroid of the appropriate potency for the condition being treated (e.g., one which is safe to apply anywhere, such as in intertriginous or genital areas, and in any age group, such as infants with diaper rash and other rashes), the provision of such a composition which promotes rapid drying of moist areas and coats the skin with the drying agent for protection and healing, the provision of such a composition which may be used to treat and cure combination rashes, i.e. fungal rashes that are associated with an irritant dermatitis, or an eczema or other dermatosis that is secondarily infected with a fungus, especially moist exudative rashes and/or rashes in moist, intertriginous areas.

Briefly, therefore, the present invention is directed to a composition for topical administration comprising (a) a corticosteroid, (b) a drying agent, and (c) an anti-fungal agent that treats both dermatophytes and yeast.

These and other objects of the present invention will be more fully understood in the light of the specific examples and description set forth below.

DETAILED DESCRIPTION OF THE PREFERRED EMBODIMENTS

The composition of the present invention may be in the form of a solution, spray, lotion, cream, gel or ointment. The preferred form of the composition depends upon the condition being treated and the desired therapeutic effect. For example, treatment of a moist, acutely inflamed rash is preferably treated with a lotion, whereas treatment of a chronic dry patch is often treated more effectively with a cream or ointment. In general, the effectiveness of the composition is directly related to the form of the composition with ointment forms of corticosteroid being stronger than gels, gels being stronger than creams, creams being stronger than lotions and solutions. For example, ointment preparations of the same corticosteroid in the same concentration are generally stronger than the cream preparation.

The lotions of the present invention include liquid suspensions and dispersions. Solid-in-liquid suspensions are preparations of finely divided, undissolved drugs or other particulate matter dispersed in liquid vehicles. These suspensions require shaking before application to ensure uniform distribution of solid in the vehicle. Liquid-in-liquid dispersions generally contain a higher water content than cream emulsions and are pourable. Lotions provide a protective, drying, and cooling effect and may act as a vehicle for other agents. The addition of alcohol increases the cooling effect. If an astringent, such as aluminum is present, it will precipitate protein and dry and seal exudating surfaces.

In a preferred embodiment, the composition of the present invention is a shake lotion containing a solid-in-liquid suspension or a liquid-in-liquid dispersion. For example, the shake lotion may be formed by combining a corticosteroid and an anti-fungal agent with a solid-in-liquid suspension or liquid-in-liquid emulsion drying lotion. In this embodiment, such compositions preferably contain at least about 15% by weight water, more preferably at least about 20%, still more preferably at least about 30%, and still more preferably about 40% to about 60% by weight water but no emulsifier. Exemplary water-based, solid-in-liquid suspensions and liquid-in-liquid emulsions include calamine lotions.

In general, preferred compositions of the present invention contain up to about 5% by weight of a corticosteriod, up to about 7% by weight of an antifungal agent, up to about 60% by weight drying agent, one or more optional ingredients (for example, one or more anti-itch agents; anti-foaming agents; buffers, neutralizing agents, and agents to adjust pH; coloring agents and decoloring agents; emollients; emulsifying agents, emulsion stabilizers and viscosity builders; humectants; odorants; preservatives, antioxidants, and chemical stabilizers; solvents; and thickening, stiffening, and suspending agents), and a balance of water or solvent.

Vehicles

Topical therapy may be delivered by any of various vehicles, typically solutions, sprays, lotions, gels, creams, and ointments, progressing in order from least to most hydrating and conversely, most to least drying. Alternatively, the composition may be delivered via a liposome, nanosome, rivosome, or nutri-diffuser vehicle. In another alternative embodiment, the vehicle is a barrier cream which comprises a hydrogel polymer such as carboxymethylcellulose, 2-hydroxyethyl methacrylate (also known as Hydron), guar gum, locust bean gum and aloe vera; hydrogels can be deposited on the skin in a water-resistant, non-gummy, hydroscopic, flexible, and pliable thin film.

The chemical composition of the vehicle may affect the bioavailability and thus, the therapeutic effectiveness of the composition. In general, acute inflammation is treated with aqueous drying preparations, and chronic inflammation is treated with hydrating preparations. Powder-in-water suspension type lotions, solutions (medications dissolved in a solvent) and gels are for hairy and intertriginous areas. Oil-in-water emulsion type lotions, creams and ointments tend to be more absorbable and more effective hydrating agents, appropriate for dry scaly eruptions, but are greasy and therefore often undesirable. In general, solutions, powder-in-water suspension type lotions, lotions and gels are preferred and, for many applications such as the treatment of contact dermatitis (e.g., diaper rash), powder-in-water lotions (sometimes referred to as "shake lotions") are particularly preferred.

Preferred vehicles of the present invention include calamine containing lotions and gels. Calamine lotions are preferably shake-lotions containing calamine, zinc oxide, glycerin, thickening agent(s), water and one or more optional ingredients identified as additional agents elsewhere herein. Calamine gels generally contain the same ingredients as the calamine lotions and are, for example, gels of water, acetone, alcohol, or propylene glycol thickened with organic polymers such as carbopols. Preferred lotions typically include calamine (about 2% to about 20% by weight, preferably about 4% to about 15% by weight, more preferably about 6% to about 10% by weight), zinc oxide (about 2% to about 20% by weight, preferably about 4% to about 15% by weight, more preferably about 6% to about 10% by weight), glycerin (about 1% to about 10% by weight, preferably about 2% to about 5% by weight), bentonite magma (about 1 to about 30% by weight, preferably about 2% to about 25% by weight), and calcium hydroxide in sterile water (to make 100% by weight). Preferred optional ingredients additionally include talc (about 2% to about 30% by weight, preferably about 5% to about 15% by weight, more preferably about 10% by weight), peanut oil (about 20% to about 80% by weight, preferably about 25% to about 75% by weight, more preferably about 50% by weight), phenol (up to about 5% by weight), alcohol (up to about 50% by weight) and tannic acid (up to about 5% by weight). Calamine gels may additionally include, for example, microcrystalline cellulose gel (about 20% to about 60% by weight, preferably about 30% to about 50% by weight, more preferably about 45% by weight), and carmellose sodium (up to about 5% by weight).

Corticosteroid

The corticosteroid preferably provides the desired therapeutic effect with little or no risk of causing atrophy of the skin, induction of telangieclasia or, in infants, suppression of hypothalamic-pituitary-adrenal axis. The corticosteroid selected and the concentration thereof in the composition, therefore, will depend, at least in part upon the therapeutic application and the vehicle selected. For example, the therapeutic effectiveness of a topical corticosteroid is related to the potency of the drug and its percutaneous penetration. Therapeutic effectiveness is thus significantly affected by the vehicle. For example, the potency of two of the stronger preparations can be modified by alteration of the corticosteroid moiety in one (clobetasol propionate) and optimization of the vehicle in the other (betamethasone dipropionate). Also, small changes in molecular structure related to enhancing the intrinsic activity of the corticosteroid moiety, increasing lipophiliciity to facilitate better skin penetration, and retarding the metabolic inactivation of the molecule result in significant alterations in clinical effectiveness. The corticosteroid, therefore, may be a high-potency, mid-potency or low-potency corticosteroid. In general, mid-potency and low-potency corticosteroids are preferred and the composition preferably contains at least about 0.0005% and typically up to about 5% by weight of the corticosteriod.

For pediatric patients and for treatment of intertriginous areas in any age group, low potency steroids are generally preferred in view of certain disadvantages of high-potency steroids. Fluorinated steroids such as betamethasone dipropionate and triamcinalone can be cutaneously dangerous to use in intertriginous regions and can cause undesirable effects including skin atrophy, rebound phenomenon and telangiectasia. If applied to large surface areas on infants, they can cause systemic effects with suppression of hypothalamic-pituitary-adrenal axis. Exemplary low-potency steroids (and concentrations expressed as a weight percentage of the composition of the present invention) include:

hydrocortisone (about 0.1% to about 5%, preferably about 0.25% to about 3.5%, more preferably about 0.5 to about 2.5% by weight);

hydrocortisone acetate (about 0.1% to about 5%, preferably about 0.25 to about 3.5%, more preferably about 0.5% to about 2.5% by weight);

cortisone (about 0.1% to about 5%, preferably about 0.25 to about 3.5%, more preferably about 0.5 to about 2.5% by weight);

prednisone acetate (about 0.025% to about 1.25%, preferably about 0.05% to about 1%, more preferably about 0.125% to about 0.75% by weight);

prednisone valerate (about 0.025% to about 1.25%, preferably about 0.05% to about 1%, more preferably about 0.125% to about 0.75% by weight);

prednisolone (about 0.025% to about 1.25%, preferably about 0.05% to about 1%, more preferably about 0.125% to about 0.75% by weight);

alclometasone dipropionate (about 0.01% to about 0.1%, preferably about 0.025% to about 0.075%, more preferably about 0.05% by weight);

dexamethasone (about 0.005% to about 1%; preferably about 0.01% to about 0.5%; more preferably about 0.05% to about 0.1% by weight);

methylprednisolone (about 0.01% to about 5%, preferably about 0.05% to about 2.5%, more preferably about 0.5% to about 1% by weight);

fluocinolone acetonide (about 0.0025 to about 0.025%, preferably about 0.005% to about 0.0125%, more preferably about 0.01% by weight); and desonide (about 0.01% to about 0.1%, preferably about 0.025% to about 0.075%, more preferably about 0.05% by weight).

Some conditions, such as severe exudative diaper rash, severe intertrigo, severe tinea infections, severe seborrhea, recalcitrant psoriasis, or forms of lichen simplex chronicus will require a mid-potency steroid for effective treatment. Exemplary mid-potency steroids include:

fluocinolone acetonide (about 0.005% to about 0.075%, preferably about 0.01% to about 0.05%, more preferably about 0.025% by weight);

prednicarbate (about 0.01% to about 0.5%, preferably about 0.05% to about 0.25%, more preferably about 0.1% by weight);

hydrocortisone butyrate (about 0.01% to about 1%; preferably about 0.05% to about 0.5%; more preferably about 0.1% by weight);

hydrocortisone propionate (about 0.01% to about 1%; preferably about 0.05% to about 0.5%; more preferably about 0.1% by weight); and hydrocortisone valerate (about 0.01% to about 1%; preferably about 0.05% to about 0.5%; more preferably about 0.2% by weight).

Some conditions in non-intertriginous areas and nonpediatric patients require a fluorinated mid-potency steroid or high-potency steroid for effective treatment. Exemplary fluorinated mid-potency steroids and high-potency steroids include:

flumethasone pivolate (about 0.005% to about 0.1%, preferably about 0.01% to about 0.05%, more preferably about 0.03% by weight);

clocortolone pivolate (about 0.01% to about 1%, preferably about 0.05% to about 0.5%, more preferably about 0.1% by weight);

triamcinolone acetonide (about 0.001% to about 1%; preferably about 0.01% to about 0.5%; more preferably about 0.025% to about 0.1% by weight);

fluticasone propionate (about 0.0005% to about 0.5%; preferably about 0.001% to about 0.1%; more preferably about 0.005% to about 0.05% by weight);

flurandrenolide (about 0.005% to about 0.5%; preferably about 0.01% to about 0.1%; more preferably about 0.025% to about 0.05% by weight);

mometasone furoate (about 0.01% to about 0.5%, preferably about 0.05% to about 0.25%, more preferably about 0.1% by weight);

desoximetasone (about 0.005% to about 1%; preferably about 0.01% to about 0.5%; more preferably about 0.05% to about 0.25% by weight);

betamethasone (about 0.005% to about 0.5%; preferably about 0.01% to about 0.25%; more preferably about 0.05% to about 0.1% by weight);

betamethasone dipropionate (about 0.005% to about 0.5%; preferably about 0.01% to about 0.1%; more preferably about 0.05% by weight);

betamethasone valerate (about 0.01% to about 0.5%, preferably about 0.05% to about 0.25%, more preferably about 0.1% by weight);

betamethasone propionate (about 0.005% to about 0.5%; preferably about 0.01% to about 0.1%; more preferably about 0.05% by weight);

betamethasone benzoate (about 0.005% to about 0.5%; preferably about 0.01% to about 0.1%; more preferably about 0.05% by weight);

diflorasone diacetate (about 0.005% to about 0.5%; preferably about 0.01% to about 0.1%; more preferably about 0.05% by weight);

fluocinonide (about 0.005% to about 0.5%; preferably about 0.01% to about 0.1%; more preferably about 0.05% by weight);

halcinonide (about 0.01% to about 0.5%, preferably about 0.05% to about 0.25%, more preferably about 0.1% by weight);

amcinonide (about 0.01% to about 0.5%, preferably about 0.05% to about 0.25%, more preferably about 0.1% by weight);

halobetasol propionate (about 0.005% to about 0.5%; preferably about 0.01% to about 0.1%; more preferably about 0.05% by weight); and clobetasol propionate (about 0.005% to about 0.5%; preferably about 0.01% to about 0.1%; more preferably about 0.05% by weight).

In general, the relative potency of topical steroids may be determined by a vasoconstrictor assay. Such assays visually measure the amount of vasoconstriction produced by the steroid with the degree of pallor produced after application of the steroid over a period of time increasing with the concentration of the steroid. See, for example, McKenzie et al., Archives of Dermatology, vol. 86, pp. 608–610 (1962); Stoughton, Archives of Dermatology, vol. 99, pp. 753–756 (1969); Place et al., Archives of Dermatology, vol. 101, pp. 531–537 (1970); Staughton, Archives of Dermatology, vol. 106, pp. 825–827 (1972); Jackson et al., Journal of the American Academy of Dermatology, vol. 20, pp. 791–796 (1989); and Staughton, Archives of Dermatology, vol. 123, pp. 1312–1314 (1987). To some extent, these assays are imprecise due to the variation between observers and other parameters within an individual study. Nevertheless, general trends emerge and the potency of a steroid may be determined by reference to the potency of other steroids which have been classified as low-potency, mid-potency, or high-potency herein. For example, the potency of a steroid may be determined in a vasoconstrictor assay of the type described by these articles with reference to the low-potency, mid-potency and high-potency corticosteroids identified herein with a corticosteroid being considered a low-potency if it produces an amount of vasoconstriction which is equivalent to the amount of vasoconstriction produced by the low-potency steroids disclosed herein. In Fitzpatrick, Thomas, D., et al., *Dermatology in General Medicine*, (4 th ed., 1993 McGraw-Hill, Inc., p. 2847), the potency ranking for a number of commonly used corticosteroids is given as determined by double-blind clinical studies and vasoconstrictor assays. In general, the corticosteroids identified as low potency corticosteroids herein fall within Groups 6 and 7 in this ranking, the corticosteroids identified as mid-potency corticosteroids herein fall within Groups 4 and 5 in this ranking and the corticosteroids identified as high-potency steroids herein fall within Groups 1, 2 and 3 of this ranking.

The composition of the present invention may contain each of the above-identified steroids in solution, spray, lotion, cream, gel or ointment form with the corticosteroid selected and the concentration thereof in the composition, depending at least in part, upon the therapeutic application and the vehicle selected.

Antifunqal

The composition of the present invention preferably contains at least about 0.1% by weight, more preferably about 0.25% to about 10%, still more preferably about 0.4% to about 7% of an antifungal agent, and, depending upon the antifungal agent, still more preferably about 1% to about 2% by weight of an antifungal agent. In general, the antifungal agent may be an imidazole antifungal agent such as miconazole, clotrimazole, butoconazole, tioconazole, econazole, ketoconazole, oxiconizole and sulconazole, a benzylamine such as butenafine HCl, allylamines such as naftifine and terbinafine, triazoles such as terconazole, hydroxypyridone agents such as ciclopirox, halogenated phenolic ethers such as haloprogin, thiocarbamates such as tolnaftate, selenium sulfide, zinc pyrithione, and other antifungal agents such as thymol and tinver. Preferably, the antifungal agent is an imidazole, and for many applications, it is preferably clotrimazole (about 0.5% to about 5%, more preferably about 1% to about 2% by weight).

Drying Agent

The drying agent generally promotes rapid drying of moist areas and coats the skin for protection and healing. In particular, it acts to prevent irritation of the involved area and water loss from the skin layer by forming a physical barrier on the skin. Preferred drying agents include calamine; zinc containing drying agents such as zinc oxide, zinc stearate and zinc sulfate; copper sulfate; kaolin; potassium permanganate; Burow's aluminum solution; talc; starches such as wheat and corn starch; silver nitrate, and acetic acid. Calamine and zinc oxide are particularly preferred.

In general, the composition of the present invention contains at least about 2.5% by weight and no more than about 60% by weight drying agent. Typically, the composition contains about 5% to about 50% by weight drying agent, and for many applications such as the treatment of contact dermatitis (e.g., diaper rash), the composition preferably contains about 7% by weight to about 25% by weight drying agent. The composition may contain a single drying agent, for example, calamine or zinc oxide, or a combination of drying agents, for example, calamine and zinc oxide, calamine and zinc stearate, or calamine and one or more starches. When the composition contains calamine and one or more other drying agents such as zinc oxide, the weight ratio of calamine to the other drying agent(s) is generally about 0.5:1 to about 10:1, respectively. For example, the weight ratio of calamine to zinc-containing drying agents will preferably be about 1:1 to about 3:1, respectively, the weight ratio of calamine to talc will preferably be about 1:1 to about 3:1, respectively, and the weight ratio of calamine to starch drying agent(s) will preferably be about 1:1 to about 10:1, respectively, in compositions containing calamine and one or more other drying agents. Calamine (which is zinc oxide with approximately 0.5% by weight ferric oxide) reduces inflammation, redness and itching, as well as promoting drying of excess oils and fluids; preferably, therefore, the composition includes calamine in an amount between about 7 and 25 weight percent and, more preferably, additionally includes zinc oxide in an amount between 7 and about 25 weight percent. A particularly preferred composition for contact dermatitis comprises calamine (about 7% to about 10% by weight) and zinc oxide (about 7% to about 10% by weight).

Additional Agents

The composition of the present invention may comprise an anti-itch agent such as phenol, camphor, menthol, benzocaine, diphenylhydramine or pramoxine. In general, the concentration of these anti-itch agents in the composition will be about 0.3 wt % to about 1 wt % for each of menthol, camphor and phenol; about 0.5 wt. % to about 20 wt % benzocaine; about 0.1 wt. % to about 20 wt %, more preferably about 0.5 wt % to about 5 wt. %, and still more preferably about 1 wt % to about 2 wt % for diphenylhydramine; and about 0.1 wt. % to about 20 wt %, more preferably about 0.5 wt % to about 5 wt. %, and still more preferably about 1 wt % for pramoxine. When an anti-itch agent is included, particularly if the anti-itch agent is diphenylhdramine or pramoxine, the composition preferably additionally comprises zinc acetate (about 0.01 wt % to about 5 wt. %, more preferably about 0.05 wt. % to about 3 wt. %, and still more preferably about 0.1 wt. % to about 1 wt. % zinc acetate).

The composition of the present invention may include a wide range of optional ingredients including, antifoaming agents; buffers, neutralizing agents and agents to adjust pH; coloring agents and decoloring agents; emollients; emulsifying agents; emulsion stabilizers and viscosity builders; humectants; odorants; preservatives, antioxidants, and chemical stabilizers; solvents; and thickening, stiffening and suspending agents. Exemplary antifoaming agents include cyclomethicone, dimethicone (e.g., dimethicone 350) and simethicone. Exemplary buffers, neutralizing agents and agents to adjust pH include ammonium hydroxide, citric acid, diisopropanolamine, hydrochloric acid, lactic acid, monobasic sodium phosphate, sodium citrate, sodium hydroxide, sodium phosphate, triethanolamine, and trolamine. Exemplary emollients include caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol and urea. Exemplary emulsifying agents include aluminum starch octenylsuccinate, ammonium hydroxide, amphoteric-9, beeswax, synthetic beeswax, carbomer 934, carbomer 934P, carbomer 940, ceteareth-20, ceteareth-30, cetearyl alcohol, ceteth 20, cetyl alcohol, cholesterol, cyclomethicone, diglycerides, dimethicone (e.g., dimethicone 350), disodium monooleamidosulfosuccinate, NF emulsifying wax, fatty acid pentaerythritol ester, glycerides, glyceryl monooleate, glyceryl monostearate, lanolin, lanolin alcohol, hydrogenated lanolin, magnesium stearate, mineral oil, monoglycerides, polyethylene glycol, PEG 100 stearate, polyethylene glycol 6000 distearate, polyethylene glycol 1000 monocetyl ether, polyethylene glycol monostearate, polyethylene glycol 400 monostearate, polyoxyethylene glycol fatty alcohol ethers, polyoxyl 20 cetostearyl ether, polyoxyl 40 stearate, polysorbate 20, polysorbate 40, polysorbate 60, polysorbate 80, polysorbates, PPG-26 oleate, propylene glycol stearate, quaternium-15, simethicone, sodium laureth sulfate, sodium lauryl sulfate, sorbitan esters, sorbitan monolaurate, sorbitan monooleate, sorbitan monopalmitate, sorbitan monostearate, sorbitan palmitate, sorbitan sesquioleate, steareth-2, steareth-100, stearic acid, stearyl alcohol, triethanolamine and trolamine. Exemplary emulsion stabilizers and viscosity builders include carbomer 934, carbomer 934P, carbomer 940, cetearyl alcohol, cetostearyl alcohol, cetyl alcohol, cetyl stearyl alcohol, dextrin, diglycerides, disodium edetate, edetate disodium, glycerides, glyceryl monostearate, glyceryl stearate, hydroxypropyl cellulose, monoglycerides, plasticized hydrocarbon gel, polyethylene glycol 300, polyethylene glycol 400, polyethylene glycol 1450, polyethylene glycol 8000, polyethylene glycols, propylene glycol stearate and stearyl alcohol. Exemplary humectants include glycerine, propylene glycol, sorbitol and urea. Exemplary odorants include hypoallergenic perfume, and menthol. Exemplary preservatives, antioxidants, and chemical stabilizers include alcohol, benzyl alcohol, butylated hydroxyanisole, butylated hydroxytoluene, butylparaben, calcium acetate, caster oil, chlorocresol, 4chloro-m-cresol, citric acid, disodium edetate, Dowicil 200 (Dow), edetate disodium, ethoxylated alcohol, ethyl alcohol, glycerin, Glydant Plus (Lonza), 1,2,6-hexanetriol, Kathon CG (Rohm & Haas), Liquid Germall Plus (ISP Sutton Labs), Liquipar (ISP Sutton Labs), methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, Ucarcide (Union Carbide), and zinc stearate. Exemplary solvents include alcohol, castor oil, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, and SD alcohol 40, triglycerides of saturated fatty acids. Exemplary thickening, stiffening and suspending agents include aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, and bentonite.

Other agents which may be added to the composition of the present invention include aloe, arachis oil, benzoic acid, cocoa butter (up to about 70% by weight); coenzyme Q10 ("ubiquinone"), eucalyptus oil, resorcinol (up to about 5% by weight); retinol; retinyl palmitate; retinyl acetate; fennel extract; whey protein; ceramide; nystatin (about 50,000 International Units per gram to about 300,000 International Units per gram, preferably about 75,000 International Units to about 125,000 International Units per gram), fungizone, amphotericin B, undecylenic acid, silicone (about 1% to about 50% by weight); alpha-hydroxy acids, beta-hydroxy acids, sorbitol, vitamin A (about 500 International Units per gram to about 300,000 International Units per gram provided, for example, in the form of fish liver oil, cod liver oil or shark liver oil), vitamin B (including panthenol and beta-carotene), vitamin C, vitamin D (about 50 International Units per gram to about 500 International Units per gram), vitamin E (about 20 International Units per gram to about 500 International Units per gram), and vitamin K. Unless otherwise indicated, the composition will generally contain less than about 5% by weight and typically less than about 1% by weight of the above-ingredients.

Treatment/Administration

The composition of the invention is applied topically to the involved area until it has healed. For example, for contact dermatitis a composition containing hydrocortisone (about 1% by weight), clotrimazole (about 1% by weight), calamine (about 8% by weight), zinc oxide (about 8% by weight), glycerin (about 2% by weight), bentonite magma (about 25% by weight) and calcium hydroxide in sterile water (to 100% by weight) is preferably administered two to four times a day for from one day to a week or more until healing occurs.

In one embodiment, the composition of the present invention comprises a nonpainful, soothing agent that will control the irritant dermatitis (e.g., a corticosteroid safe to use under occlusion, on an infant, on genital and intertriginous skin), that will eradicate the secondary Candida infection (e.g., an antifungal agent), and that will dry the area while providing a barrier (e.g., calamine). In addition, it can effectively provide fast relief of symptoms and eradication of the fungal infection while minimizing the risk of undesirable side effects caused by high-potency and/or fluorinated steroids.

For such uses, the composition preferably contains a (i) low-potency steroid such as hydrocortisone, hydrocortisone acetate, alclometasone dipropionate, fluocinolone acetonide, dexamethasone, methylprednisolone or desonide, (ii) an anti-fungal such as miconazole, clotrimazole, ketoconazole, oxiconizole, butenafine HCl, naftifine, terbinafine, ciclopirox, tolnaftate, and (iii) a drying agent such as a calamine containing lotion or gel. For such uses, the composition more preferably contains a (i) low-potency steroid such as hydrocortisone, alclometasone dipropionate, or desonide, (ii) an anti-fungal such as miconazole, clotrimazole, ketoconazole, oxiconizole, terbinafine, tolnaftate, and (iii) a drying agent such as a calamine, and is in the form of a lotion or gel. For such uses, the composition still more preferably contains (i) hydrocortisone, (ii) miconazole, clotrimazole, ketoconazole, terbinafine, or tolnaftate, and (iii) a drying agent such as a calamine containing lotion or gel. The concentration of the low-potency steroid in these compositions is preferably about 0.25% to about 3.5% by weight, more preferably about 0.5% to about 2.5% by weight for hydrocortisone and hydrocortisone acetate; preferably about 0.025% to about 0.075% by weight and more preferably about 0.05% for alclometasone dipropionate and desonide; and preferably about 0.005% to about 0.0125% by weight and more preferably about 0.01% for fluocinolone acetonide. The concentration of the anti-fungal agents in these compositions is about 0.5% to about 5% and more preferably about 1% to about 2% by weight for miconazole, clotrimazole, ketoconazole, oxiconizole, butenafine HCl, naftifine, terbinafine, ciclopirox, and tolnaftate.

In another embodiment, for conditions such as severe exudative diaper rash, severe intertrigo, severe tinea infections, severe seborrhea, recalcitrant psoriasis, or forms of lichen simplex chronicus, the composition will include a mid-potency steroid for more effective treatment. For such uses, the composition preferably contains (i) a mid-potency steroid such as hydrocortisone butyrate, hydrocortisone valerate, or prednicarbate, (ii) an anti-fungal such as miconazole, clotrimazole, ketoconazole, oxiconizole, butenafine HCl, naftifine, terbinafine, ciclopirox, tolnaftate, and (iii) a drying agent such as a calamine, and is in the form of a lotion or gel. For such uses, the composition more preferably comprises (i) a midpotency steroid such as hydrocortisone butyrate or hydrocortisone valerate, (ii) an anti-fungal such as miconazole, clotrimazole, ketoconazole, oxiconizole, terbinafine, tolnaftate, and (iii) a drying agent such as a calamine containing lotion or gel. For such uses, the composition still more preferably contains (i) hydrocortisone valerate, (ii) miconazole, clotrimazole, ketoconazole, terbinafine, or tolnaftate, and (iii) a drying agent such as a calamine containing lotion or gel. The concentration of hydrocortisone butyrate and hydrocortisone valerate in such compositions is preferably about 0.05% to about 0.5% and more preferably about 0.1 to about 0.2% by weight. The concentration of the prednicarbate is preferably about 0.01% to about 0.5%, more preferably about 0.05% to about 0.25%, more preferably about 0.1% by weight. The concentration of the anti-fungal agents in these compositions is about 0.5% to about 5% and more preferably about 1% to about 2% by weight for miconazole, clotrimazole, ketoconazole, oxiconizole, butenafine HCl, naftifine, terbinafine, ciclopirox, and tolnaftate.

In still another embodiment, for conditions such as very severe and recalcitrant exudative diaper rash, intertrigo, tinea infections, seborrhea,psoriasis or licehn simplex chronicus, the composition preferably includes a fluorinated mid-potency steroid or high-potency steroid for more effective treatment; it should be noted, however, that fluorinated steroids are generally safe for diaper rash and intertrigo if used for relatively brief periods. For such uses, the composition is preferably in the form of a lotion or gel and it contains (i) a drying agent such as calamine, (ii) an anti-fungal such as miconazole, clotrimazole, ketoconazole, oxiconizole, butenafine HCL, naftifine, terbinafine, ciclopirox, tolnaftate, and (iii) a fluorinated mid-potency or high-potency steroid such as

- triamcinolone acetonide (about 0.001% to about 1%; preferably about 0.01% to about 0.5%; more preferably about 0.025% to about 0.1% by weight);
- fluticasone propionate (about 0.0005% to about 0.5%; preferably about 0.001% to about 0.1%; more preferably about 0.005% to about 0.05% by weight);
- flurandrenolide (about 0.005% to about 0.5%; preferably about 0.01% to about 0.1%; more preferably about 0.025% to about 0.05% by weight);
- mometasone furoate (about 0.01% to about 0.5%, preferably about 0.05% to about 0.25%, more preferably about 0.1% by weight);
- desoximetasone (about 0.005% to about 1%; preferably about 0.01% to about 0.5%; more preferably about 0.05% to about 0.25% by weight);
- betamethasone (about 0.005% to about 0.5%; preferably about 0.01% to about 0.25%; more preferably about 0.05% to about 0.1% by weight);
- betamethasone dipropionate (about 0.005% to about 0.5%; preferably about 0.01% to about 0.1%; more preferably about 0.05% by weight);
- betamethasone valerate (about 0.01% to about 0.5%, preferably about 0.05% to about 0.25%, more preferably about 0.1% by weight);
- betamethasone propionate (about 0.005% to about 0.5%; preferably about 0.01% to about 0.1%; more preferably about 0.05% by weight);
- betamethasone benzoate (about 0.005% to about 0.5%; preferably about 0.01% to about 0.1%; more preferably about 0.05% by weight);
- diflorasone diacetate (about 0.005% to about 0.5%; preferably about 0.01% to about 0.1%; more preferably about 0.05% by weight);
- fluocinonide (about 0.005% to about 0.5%; preferably about 0.01% to about 0.1%; more preferably about 0.05% by weight);
- halcinonide (about 0.01% to about 0.5%, preferably about 0.05% to about 0.25%, more preferably about 0.1% by weight);
- amcinonide (about 0.01% to about 0.5%, preferably about 0.05% to about 0.25%, more preferably about 0.1% by weight);
- halobetasol propionate (about 0.005% to about 0.5%; preferably about 0.01% to about 0.1%; more preferably about 0.05% by weight); and
- clobetasol propionate (about 0.005% to about 0.5%; preferably about 0.01% to about 0.1%; more preferably about 0.05% by weight).

For such uses, the composition more preferably comprises (i) a drying agent such as calamine, (ii) an anti-fungal such as miconazole, clotrimazole, ketoconazole, oxiconizole, terbinafine, and tolnaftate, and (iii) a fluorinated mid-potency or high-potency steroid such as

- triamcinolone acetonide (about 0.001% to about 1%; preferably about 0.01% to about 0.5%; more preferably about 0.025% to about 0.1% by weight);
- fluticasone propionate (about 0.0005% to about 0.5%; preferably about 0.001% to about 0.1%; more preferably about 0.005% to about 0.05% by weight);
- mometasone furoate (about 0.01% to about 0.5%, preferably about 0.05% to about 0.25%, more preferably about 0.1% by weight);
- desoximetasone (about 0.005% to about 1%; preferably about 0.01% to about 0.5%; more preferably about 0.05% to about 0.25% by weight);
- betamethasone (about 0.005% to about 0.5%; preferably about 0.01% to about 0.25%; more preferably about 0.05% to about 0.1% by weight);
- betamethasone dipropionate (about 0.005% to about 0.5%; preferably about 0.01% to about 0.1%; more preferably about 0.05% by weight);
- betamethasone valerate (about 0.01% to about 0.5%, preferably about 0.05% to about 0.25%, more preferably about 0.1% by weight);
- betamethasone propionate (about 0.005% to about 0.5%; preferably about 0.01% to about 0.1%; more preferably about 0.05% by weight);
- betamethasone benzoate (about 0.005% to about 0.5%; preferably about 0.01% to about 0.1%; more preferably about 0.05% by weight);
- diflorasbne diacetate (about 0.005% to about 0.5%; preferably about 0.01% to about 0.1%; more preferably about 0.05% by weight);
- fluocinonide (about 0.005% to about 0.5%; preferably about 0.01% to about 0.1%; more preferably about 0.05% by weight);
- halobetasol propionate (about 0.005% to about 0.5%; preferably about 0.01% to about 0.1%; more preferably about 0.05% by weight); and
- clobetasol propionate (about 0.005% to about 0.5%; preferably about 0.01% to about 0.1%; more preferably about 0.05% by weight).

For such uses, the composition still more preferably comprises (i) a drying agent such as calamine, (ii) an anti-fungal such as miconazole, clotrimazole, ketoconazole, terbinafine, or tolnaftate, and (iii) a fluorinated mid-potency or high-potency steroid such as

- triamcinolone acetonide (about 0.001% to about 1%; preferably about 0.01% to about 0.5%; more preferably about 0.025% to about 0.1% by weight);
- desoximetasone (about 0.005% to about 1%; preferably about 0.01% to about 0.5%; more preferably about 0.05% to about 0.25% by weight);
- betamethasone (about 0.005% to about 0.5%; preferably about 0.01% to about 0.25%; more preferably about 0.05% to about 0.1% by weight);
- betamethasone dipropionate (about 0.005% to about 0.5%; preferably about 0.01% to about 0.1%; more preferably about 0.05% by weight);
- betamethasone valerate (about 0.01% to about 0.5%, preferably about 0.05% to about 0.25%, more preferably about 0.1% by weight);
- betamethasone propionate (about 0.005% to about 0.5%; preferably about 0.01% to about 0.1%; more preferably about 0.05% by weight);
- betamethasone benzoate (about 0.005% to about 0.5%; preferably about 0.01% to about 0.1%; more preferably about 0.05% by weight);
- diflorasone diacetate (about 0.005% to about 0.5%; preferably about 0.01% to about 0.1%; more preferably about 0.05% by weight);

fluocinonide (about 0.005% to about 0.5%; preferably about 0.01% to about 0.1%; more preferably about 0.05% by weight); and clobetasol propionate (about 0.005% to about 0.5%; preferably about 0.01% to about 0.1%; more preferably about 0.05% by weight).

The concentration of the anti-fungal agents in these compositions for conditions such as very severe and recalcitrant exudative diaper rash is about 0.5% to about 5% and more preferably about 1% to about 2% by weight for miconazole, clotrimazole, ketoconazole, oxiconizole, butenafine HCl, naftifine, terbinafine, ciclopirox, and tolnaftate.

One of the problems with the prior creams containing nystatin and hydrocortisone is that the antifungal coverage is not as broad spectrum as with an imidazole antifungal agent like miconazole or clotrimazole. Nystatin and other polyene antibiotics only treat yeast (Candida) infections, while the azole (imidazole) compounds treat both dermatophytes and yeast (Arndt, Kenneth A., *Manual of Dermatologic Therapeutics*, $5^{th}$ edition, 1995, Little, Brown and Co., page 290). In mixed infections, therefore, where dermatophyte infections are present, the composition containing hydrocortisone and nystatin will not provide the desired full spectrum of activity while the imidazole antifungals will, while still treating the Candida. The proposed invention will also treat tinea cruis, tinea pedis (interdigital type), tinea corporis and tinea versicolar. Nystatin will not treat these entities.

The following examples illustrate the invention.

CLINICAL EXAMPLES

Composition A: Hydrocortisone 1%
   Clotrimazole 1%
   Calamine lotion 98%
Composition B: Hydrocortisone 1%
   Clotrimazole 2%
   Calamine lotion 97%
Composition C: Hydrocortisone 0.5%
   Clotrimazole 1%
   Calamine lotion 98.5%
Calamine Lotion Calamine (U.S.P.)—8 gm
   Zinc oxide—8 gm
   Glycerin—2 ml
   Bentonite magma—25 ml
   Calcium hydroxide in sterile water—to 100 ml Two infants presented with diaper rash. The first, an 18-month-old (Dv) had the rash for about 1 week, and 1% clotrimazole cream was not helping. He had multiple red papules, confluent in areas into patches, located mainly on the suprapubic and perineal areas. After 1 day of using composition A (2 or 3 applications) the rash was clear. The second, a 3 year old, presented with red patches and papules in his groin, present for 2 weeks. The rash improved greatly after 6 days of use. The mother was so satisfied that she called for a refill 2 months later for another episode of the diaper dermatitis.

Seventeen patients presented with intertrigo. In general, the patients responded well to composition A. One patient (A. H.) had a pruritic genital rash for 4 years, consisting of diffuse erythema located on both upper inner thighs, within her groin and gluteal cleft. She did not clear with Vytone 1% hydrocortisone, hydrocortisone 0.5% combined with Nizoral cream, or plain Nizoral cream at night with Zeasorb powder in the morning. She was prescribed composition A. Within 5 weeks she showed marked improvement. A 14 year old girl (D. B.) presented with more than a month of a pruritic, beefy red, scaly rash on her genitalia that had not responded to hydrocortisone 1% cream along with Zeasorb powder, or to Tinactin. A culture for yeast was negative. After using composition A for 9 days the genital rash was clear. Another patient (J. H.) had a pruritic genital rash for a few days. Potent fluorinated topical steroids provided no relief. Composition A provided rapid relief. A 69 year old female (B. J.) had a pruritic, malodorous rash in her groin for more than 5 years. A culture taken 5 years previously grew trichophyton rubrum fungus. On exam she had erythematous macules of both inguinal folds. This was consistent with intertrigo. She used Composition A and did not need to return for follow-up. A man (P. K.) had inguinal intertrigo for several years, treated with many different agents with only temporary success. When prescribed composition A, he had rapid improvement, and the composition A cleared the inguinal intertrigo after 2 months of therapy. He subsequently developed a Candida infection on his scrotum, which also cleared with composition A. A male patient (D. K.) had a persistent groin rash, culture positive tinea cruris that did not clear after 6 weeks of Oxistat (oxiconalole) treatment. On exam he had diffuse erythema of both groin, consistent with intertrigo. The rash improved when he used composition A, but recurred when stopped. When persuaded to use the medicine twice daily every day, he cleared after 1 month of therapy. Three months later he returned with a flare of his rash, complaining of rawness and blisters. He had macular erythema in his left groin, and an erythematous patch with papulo-pustules. A culture revealed Candida infection. Composition A provided good improvement after 1 month of use. Another patient had an extremely sore perianal rash, beefy red with a few erosions, which failed to respond to Lotrisone, Spectazole or Des Owen creams. The eruption showed dramatic improvement after 2 weeks of using composition A. A 47 year old female (K. S.) had a very pruritic rash under her breasts that failed to respond to 2 weeks of Spectazole cream at night and Zeasorb powder in the morning. Composition A provided rapid relief. Another female (J. Z.) with a very pruritic erythematous rash under her breasts and in her groin (intertrigo) cleared in less than 2 weeks of using composition A, and stated "the medication was easy to use." A 28 year old man (K. H.) with a fungal culture negative groin rash of uncertain nature responded well to Composition B (containing 2% clotrimazole).

One patient presented with balanoposthitis. The patient (G. M.) had a red glistening shiny patch on his glans penis, consistent with both balanoposthitis and a psoriasiform dermatitis. He had a chronic rash on his penis for 5 years, which did not clear after circumcision. Composition A cleared the rash in less than a month.

Four patients presented with scrotal lichen simplex chronicus (AKA scrotodynia, male itch). An 84-year old man (J. P.) had a longstanding pruritic eruption on his scrotum, with a biopsy showing a chronic eczema, consistent with lichen simplex chronicus (LSC). Cutivate (fluticasone propionate) helped, but the rash recurred when he stopped the medication. Micatin was without help. On exam he had a thickened red patch on his scrotum. Composition A cleared the eczema after only 2–3 days of twice daily use, and remained clear for almost 2 months. Another patient (D. S.) presented with a burning and pruritic red rash on his scrotum, present for almost 5 months. Nizoral cream was without benefit. Composition A provided marked improvement after 6 weeks of therapy.

Four patients had the combination of seborrheic dermatitis and psoriasis (sebo-psoriasis). A 42 year old man (K. H.) had a chronic pruritic erythematous rash on his scrotum, penis, and within the gluteal cleft. Composition A provided good relief, with control of the eruption when used only every other day. Spectazole cream had been without benefit.

Composition C was tried, with equally good results compared to using Composition A. Another patient (W. P.) had a pruritic rash in his groin and buttocks for a period of 2–3 years that would wax and wane. On exam he had dusky red scaly patches in his groin and gluteal cleft. After one month of using composition A twice daily, he was much better. A patient with sebo-psoriasis and intertrigo (J. L.) failed to respond to a combination of 1% hydrocortisone plus Nizoral cream or to a combination of 2% hydrocortisone plus Nizoral cream. When prescribed composition A, after 1 month he stated the new compound was better. On physical exam he was much improved. After 2 months of twice daily therapy, he was totally clear. So the addition of calamine to the hydrocortisone and imidazole made the difference.

One patient (S. H.) presented with tinea versicolar on her neck, confirmed by microscopic KOH examination of skin scrapings. On return exam 19 days later the neck was clear.

One patient (T. M.) with a past history of tinea cruris presented with a 2 month flare of his groin rash. Topicort (desoximetasone) cream was without help. On exam he had beefy-red, slightly scaly patches on both upper inner thighs, extending into the groin. KOH microscopic exam revealed hyphal elements, and fungal culture grew the dermatophyte Trichophyton mentagrophytes. Composition A applied twice daily cleared the infection within 6 weeks (and possibly sooner; we had to call the patient for follow-up after 6 weeks).

What is claimed is:

1. A composition for topical administration consisting essentially of (a) a corticosteroid, (b) a broad spectrum anti-fungal agent that treats both dermatophytes and yeast, and (c) a drying agent selected from the group consisting of calamine, zinc containing drying agents, copper sulfate, kaolin, potassium permanganate, Burow's aluminum solution, talc, starch, silver nitrate, and acetic acid.

2. The composition of claim 1 wherein the corticosteroid is a low potency corticosteroid and the low potency corticosteroid is about 0.1% to about 5% by weight of the composition.

3. The composition of claim 2 wherein the low potency steroid is selected from the group consisting of hydrocortisone, hydrocortisone acetate, cortisone, prednisone acetate, prednisone valerate, prednisolone, alclometasone dipropionate, fluocinolone acetonide, dexamethasone, methylprednisolone, and desonide.

4. The composition of claim 1 wherein the corticosteroid is a mid-potency corticosteroid and the mid-potency corticosteroid is about 0.005% to about 0.1% by weight of the composition.

5. The composition of claim 4 wherein the mid-potency steroid is selected from the group consisting of fluocinolone acetonide, hydrocortisone butyrate, hydrocortisone propionate, hydrocortisone valerate, and prednicarbate.

6. The composition of claim 1 wherein the corticosteroid is a mid-potency or a high potency corticosteroid and the mid-potency or high potency corticosteroid is about 0.0005% to about 0.5% by weight of the composition.

7. The composition of claim 6 wherein the mid-potency or high potency corticosteroid is selected from the group consisting of flumethasone pivolate, clocortolone pivolate, triamcinolone acetonide, prednicarbate, fluticasone propionate, flurandrenolide, mometasone furoate, desoximetasone, betamethasone, betamethasone dipropionate, betamethasone valerate, betamethasone propionate, betamethasone benzoate, diflorasone diacetate, fluocinonide, halcinonide, amcinonide, halobetasol propionate, and clobetasol propionate.

8. The composition of claim 1 wherein the antifungal agent is at least 0.1% by weight of the composition.

9. The composition of claim 8 wherein the antifungal agent is an imidazole antifungal agent and the imidazole antifungal agent is about 0.4% to about 7% by weight of the composition.

10. The composition of claim 8 wherein the antifungal agent is clotrimazole.

11. The composition of claim 1 wherein the drying agent is calamine or a zinc-containing drying agent.

12. The composition of claim 11 wherein the corticosteroid is a low potency corticosteroid and the low potency corticosteroid is about 0.1% to about 5% by weight of the composition.

13. The composition of claim 12 wherein the antifungal agent is an imidazole antifungal agent and the imidazole antifungal agent is about 0.25% to about 10% by weight of the composition.

14. The composition of claim 11 wherein the corticosteroid is a mid-potency or high potency corticosteroid and the mid-potency or high potency corticosteroid is about 0.0005% to about 0.5% by weight of the composition.

15. The composition of claim 14 wherein the antifungal agent is an imidazole antifungal agent and the imidazole antifungal agent is about 0.25% to about 10% by weight of the composition.

16. The composition of claim 1 wherein calamine and zinc oxide are the drying agent and the weight ratio of calamine to zinc oxide is about 0.5:1 to about 10:1.

17. The composition of claim 16 wherein the corticosteroid is a low potency corticosteroid and the low potency corticosteroid is about 0.1% to about 5% by weight of the composition.

18. The composition of claim 17 wherein the antifungal agent is an imidazole antifungal agent and the imidazole antifungal agent is about 0.4% to about 7% by weight of the composition.

19. The composition of claim 16 wherein the antifungal agent is an imidazole antifungal agent and the imidazole antifungal agent is about 0.4% to about 7% by weight of the composition.

20. The composition of claim 1 wherein the composition is in the form of a shake lotion, gel or spray.

21. A composition for topical administration consisting essentially of (a) a corticosteroid, (b) a broad spectrum anti-fungal agent that treats both dermatophytes and yeast wherein the antifungal agent is selected from the group consisting of benzylamines, allylamines, triazoles, hydroxypyridone agents, halogenated phenolic ethers, and thiocarbamates, and (c) a drying agent selected from the group consisting of calamine, zinc containing drying agents, copper sulfate, kaolin, potassium permanganate, Burow's aluminum solution, talc, starch, silver nitrate, and acetic acid.

22. A composition for topical administration, the composition being a powder-in-water suspension in the form of a shake lotion, comprising (a) a corticosteroid, (b) a broad spectrum anti-fungal agent that treats both dermatophytes and yeast, and (c) a drying agent.

23. The composition of claim 22 wherein the composition contains about 0.005% to about 0.1% by weight of a mid potency corticosteroid.

24. The composition of claim 22 wherein the composition comprises at least 0.1% by weight of said antifungal agent.

25. The composition of claim 22 wherein the composition comprises about 0.4% to about 7% by weight of an imidazole anti-fungal agent.

26. The composition of claim 25 wherein the antifungal agent is clotrimazole.

27. The composition of claim 22 wherein the composition contains about 0.1% to about 5% by weight of a low potency corticosteroid.

28. The composition of claim 27 wherein the composition comprises about 0.25% to about 10% by weight of an imidazole antifungal agent.

29. The composition of claim 22 wherein the composition contains about 0.0005% to about 0.5% by weight of a mid-potency or high potency corticosteroid.

30. The composition of claim 29 wherein the composition comprises about 0.25% to about 10% by weight of an imidazole antifungal agent.

31. The composition of claim 22 wherein the composition comprises two or more drying agents, one of the drying agents is calamine, another is zinc oxide and the weight ratio of calamine to zinc oxide is about 0.5:1 to about 10:1.

32. The composition of claim 31 wherein the composition contains about 0.1% to about 5% by weight of a low potency corticosteroid.

33. The composition of claim 31 wherein the composition comprises about 0.4% to about 7% by weight of an imidazole antifungal agent.

34. The composition of claim 31 wherein the composition comprises about 0.4% to about 7% by weight of an imidazole antifungal agent.

35. The composition of claim 34 wherein the composition additionally comprises an anti-dermatophyte agent without anti-yeast efficacy.

36. The composition of claim 22 wherein the composition additionally comprises an anti-itch agent selected from the group consisting of menthol, camphor, phenol, benzocaine, diphenylhydramine, and pramoxine.

37. A composition for topical administration, the composition being a powder-in-water suspension in the form of a shake lotion, comprising (a) a corticosteroid, (b) a broad spectrum anti-fungal agent that treats both dermatophytes and yeast, and (c) a drying agent wherein the antifungal agent is selected from the group consisting of benzylamines, allylamines, triazoles, hydroxypyridone agents, halogenated phenolic ethers, and thiocarbamates.

38. The composition of claim 37 wherein the composition contains about 0.1% to about 5% by weight of a low potency corticosteroid.

39. The composition of claim 37 wherein the composition contains about 0.0005% to about 0.5% by weight of a mid-potency or high potency corticosteroid.

40. A composition for topical administration in the form of a shake lotion, gel or spray, the composition consisting essentially of (i) a corticosteroid, (ii) a broad spectrum anti-fungal agent that treats both dermatophytes and yeast, (iii) a drying agent selected from the group consisting of calamine, zinc containing drying agents, copper sulfate, kaolin, potassium permanganate, Burow's aluminum solution, talc, starch, silver nitrate, and acetic acid, and (iv) a component selected from the group consisting of:
 (a) an antifoaming agent selected from the group consisting of cyclomethicone, dimethicone and simethicone;
 (b) a buffer, neutralizing agent or agent to adjust pH selected from the group consisting of ammonium hydroxide, citric acid, diisopropanolamine, hydrochloric acid, lactic acid monobasic sodium phosphate, sodium citrate, sodium hydroxide, sodium phosphate, triethanolamine, and trolamine;
 (c) an emollient selected from the group consisting of caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol and urea;
 (d) an emulsifying agent selected from the group consisting of aluminum starch octenylsuccinate, ammonium hydroxide, amphoteric-9, beeswax, synthetic beeswax, carbomer 934, carbomer 934P, carbomer 940, ceteareth-20, ceteareth-30, cetearyl alcohol, ceteth 20, cetyl alcohol, cholesterol, cyclomethicone, diglycerides, dimethicone, disodium monooleamidosulfosuccinate, NF emulsifying wax, fatty acid pentaerythritol ester, glycerides, glyceryl monooleate, glyceryl monostearate, lanolin, lanolin alcohol, hydrogenated lanolin, magnesium stearate, mineral oil, monoglycerides, polyethylene glycol, PEG 100 stearate, polyethylene glycol 6000 distearate, polyethylene glycol 1000 monocetyl ether, polyethylene glycol monostearate, polyethylene glycol 400 monostearate, polyoxyethylene glycol fatty alcohol ethers, polyoxyl 20 cetostearyl ether, polyoxyl 40 stearate, polysorbate 20, polysorbate 40, polysorbate 60, polysorbate 80, polysorbates, PPG-26 oleate, propylene glycol stearate, quaternium-15, simethicone, sodium laureth sulfate, sodium lauryl sulfate, sorbitan esters, sorbitan monolaurate, sorbitan monooleate, sorbitan monopalmitate, sorbitan monostearate, sorbitan paimitate, sorbitan sesquioleate, steareth-2, steareth-100, stearic acid, stearyl alcohol, triethanolamine and trolamine;
 (e) an emulsion stabilizer or viscosity builder selected from the group consisting of carbomer 934, carbomer 934P, carbomer 940, cetearyl alcohol, cetostearyl alcohol, cetyl alcohol, cetyl stearyl alcohol, dextrin, diglycerides, disodium edetate, edetate disodium, glycerides, glyceryl monostearate, glyceryl stearate, hydroxypropyl cellulose, monoglycerides, plasticized hydrocarbon gel, polyethylene glycol 300, polyethylene glycol 400, polyethylene glycol 1450, polyethylene glycol 8000, polyethylene glycols, propylene glycol stearate and stearyl alcohol;
 (f) a humectant selected from the group consisting of glycerine, propylene glycol, sorbitol and urea;
 (g) an odorant selected from the group consisting of hypoallergenic perfume and menthol;
 (h) a preservative, antoxidant, or chemical stabilizer selected from the group consisting of alcohol, benzyl alcohol, butylated hydroxyanisole, butylated hydroxytoluene, butylparaben, calcium acetate, caster oil, chlorocresol, 4-chloro-m-cresol, citric acid, disodium edetate, edetate disodium, ethoxylated alcohol, ethyl alcohol, glycerin, 1,2,6-hexanetriol, methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, and zinc stearate;
 (i) a solvent selected from the group consisting of alcohol, castor oil, diisopropyl adipate, ethoxylated alcohol, ethyl alcohol, fatty alcohol citrate, glycerin, 1,2,6 hexanetriol, hexylene glycol, isopropyl alcohol, isopropyl myristate, isopropyl palnltate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, SD alcohol 40, and triglycerides of saturated fatty acids;

j) a thickening, stiffening or suspending agent selected from the group consisting of aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, and bentonite; or and (k) an additive selected from the group consisting of aloe, arachis oil, benzoic acid, camphor, cocoa butter, coenzyme Q10, eucalyptus oil, retinol, retinyl paimitate, retinyl acetate, fennel extract, whey protein, ceramide, silicone, alpha-hydroxy acids, beta-hydroxy acids, sorbitol, vitamin A, vitamin B, vitamin C, vitamin D, vitamin E, and vitamin K.

41. A composition for topical administration the composition being a powder-in-water, suspension in the form of a shake lotion; comprising (a) a corticosteriod, (b) a broad spectrum anti-fungal agent that treats both dermatophytes and yeast, and (c) a drying agent selected from the group consisting of calamine, zinc containing drying agents and mixtures thereof.

42. The composition of claim 41 wherein the composition contains about 0.1% to about 5% by weight of a low potency corticosteroid.

43. The composition of claim 41 wherein the composition contains about 0.1% to about 5% by weight of a low potency corticosteroid selected from the group consisting of hydrocortisone, hydrocortisone acetate, cortisone, prednisone acetate, prednisone valerate, prednisolone, alclometasone dipropionate, fluocinolone acetonide, dexamethasone, methylprednisolone, and desonide.

44. The composition of claim 43 wherein the composition comprises about 0.25% to about 10% by weight of an imidazole antifungal agent.

45. The composition of claim 43 wherein the composition comprises about 0.25% to about 10% by weight of clotrimazole.

46. The composition of claim 41 wherein the composition contains about 0.1% to about 5% by weight of a low potency corticosteroid and about 0.25% to about 10% by weight of an imidazole antifungal agent.

47. The composition of claim 41 wherein the composition contains about 0.1% to about 5% by weight of a low potency corticosteroid and about 0.25% to about 10% by weight clotrimazole.

48. The composition of claim 41 wherein the composition comprises calamine and zinc oxide and the weight ratio of calamine to zinc oxide is about 0.5:1 to about 10:1.

49. The composition of claim 41 wherein the composition contains about 0.1% to about 5% by weight of a low potency corticosteroid and the composition comprises calamine and zinc oxide with the weight ratio of calamine to zinc oxide being about 0.5:1 to about 10:1.

50. The composition of claim 41 wherein the composition comprises calamine and zinc oxide with the weight ratio of calamine to zinc oxide being about 0.5:1 to about 10:1 and the composition comprises about 0.1% to about 5% by weight of a low potency corticosteroid selected from the group consisting of hydrocortisone, hydrocortisone acetate, cortisone, prednisone acetate, prednisone valerate, prednisolone, alclometasone dipropionate, fluocinolone acetonide, dexamethasone, methylprednisolone, and desonide.

51. The composition of claim 44 wherein the composition comprises calamine and zinc oxide and the weight ratio of calamine to zinc oxide is about 0.5:1 to about 10:1.

52. The composition of claim 45 wherein the composition comprises calamine and zinc oxide and the weight ratio of calamine to zinc oxide is about 0.5:1 to about 10:1.

53. The composition of claim 41 wherein the composition contains about 0.1% to about 5% by weight of a low potency corticosteroid, about 0.25% to about 10% by weight of an imidazole antifungal agent, calamine and zinc oxide with the weight ratio of calamine to zinc oxide being about 0.5:1 to about 10:1.

54. The composition of claim 41 wherein the composition contains about 0.1% to about 5% by weight of a low potency corticosteroid, about 0.25% to about 10% by weight clotrimazole, calamine and zinc oxide with the weight ratio of calamine to zinc oxide being about 0.5:1 to about 10:1.

55. The composition of claim 41 wherein the composition comprises about 0.25% to about 10% by weight of an imidazole antifungal agent.

56. The composition of claim 41 wherein the composition comprises about 0.25% to about 10% by weight of an imidazole antifungal agent and the imidazole antifungal agent is clotrimazole.

57. The composition of claim 41 wherein the composition comprises about 0.25% to about 10% by weight clotrimazole, calamine and zinc oxide with the weight ratio of calamine to zinc oxide being about 0.5:1 to about 10:1.

* * * * *

UNITED STATES PATENT AND TRADEMARK OFFICE
CERTIFICATE OF CORRECTION

PATENT NO. : 6,656,928 B1  
DATED : December 2, 2003  
INVENTOR(S) : Michael E. McCadden It is certified that error appears in the above-identified patent and that said Letters Patent is hereby corrected as shown below:

Column 19,
Line 22, "claim 31" should read -- claim 32 --.

Column 20,
Lines 34-35, "sorbitan paimitate" should read -- sorbitan palmitate --.

Column 21,
Line 3, "isopropyl palnltate" should read -- isopropyl palmitate --.
Lines 21-22, "bentonite; or and" should read -- bentonite; and --.
Line 25, "retinyl paimitate" should read -- retinyl palmitate --.

Signed and Sealed this

Fifteenth Day of June, 2004

JON W. DUDAS
*Acting Director of the United States Patent and Trademark Office*